United States Patent [19]

Mudge et al.

[11] Patent Number: 5,501,851
[45] Date of Patent: Mar. 26, 1996

[54] EMULSION POLYMERS FOR USE IN HAIR FIXATIVES

[75] Inventors: Paul R. Mudge, Belle Mead; John C. Leighton, Flanders; Sirisoma Wanigatunga, Bridgewater; Natalie Morawsky, Highland Park, all of N.J.

[73] Assignee: National Starch and Chemical Investment Holding Corporation, Wilmington, Del.

[21] Appl. No.: 304,618

[22] Filed: Sep. 12, 1994

Related U.S. Application Data

[63] Continuation of Ser. No. 915,488, Jul. 16, 1992, abandoned.
[51] Int. Cl.⁶ .................. A61K 7/11; A61K 9/10; C08J 3/05; C08F 6/24
[52] U.S. Cl. .................. 424/70.16; 424/70.122; 424/78.18; 424/DIG. 1; 424/DIG. 2; 424/47; 424/501; 524/832; 524/833; 524/831
[58] Field of Search ............... 424/78.03, 78.18, 424/47, DIG.1, DIG. 2, 70, 71, 70.122

[56] References Cited

U.S. PATENT DOCUMENTS

| | | | |
|---|---|---|---|
| 2,996,471 | 8/1961 | Reiter et al. | 260/33.4 |
| 3,574,822 | 4/1971 | Shepherd et al. | 424/47 |
| 3,660,561 | 5/1972 | Shepherd et al. | 424/47 |
| 3,810,977 | 5/1974 | Levine et al. | 424/47 |
| 3,927,199 | 12/1975 | Micchelli et al. | 424/47 |
| 4,192,861 | 3/1980 | Micchelli et al. | 424/47 |
| 4,196,190 | 4/1980 | Gehman et al. | 424/47 |
| 4,315,910 | 2/1982 | Nowak, Jr. et al. | 424/47 |
| 4,798,721 | 1/1989 | Yahagi et al. | 424/70 |
| 4,842,852 | 6/1989 | Nowak, Jr. et al. | 424/47 |
| 4,961,921 | 10/1990 | Chuang et al. | 424/47 |
| 4,985,239 | 1/1991 | Yahagi et al. | 424/70 |
| 5,021,238 | 6/1991 | Martino et al. | 424/47 |
| 5,068,099 | 11/1991 | Sramek | 424/47 |
| 5,094,838 | 3/1992 | Benson et al. | 424/47 |
| 5,176,898 | 1/1993 | Goldberg et al. | 424/47 |

FOREIGN PATENT DOCUMENTS

| | | |
|---|---|---|
| 677267 | 9/1966 | Belgium . |
| 274086 | 7/1988 | European Pat. Off. . |
| 445714 | 9/1991 | European Pat. Off. . |
| 2697160 | 10/1992 | France . |
| 2098226 | 11/1982 | United Kingdom . |
| 2136689 | 9/1984 | United Kingdom . |

OTHER PUBLICATIONS

Seifen–Ole–Fette–Wachse, vol. 108, No. 13, Aug. 12, 1982, pp. 393–395, H. Bronnsack et al., "Moderne Haarsprays Marketing, Trends und Formulierungstechnick".

Seifen–Ole–Fette–Wachse, vol. 117, No. 13, Aug. 28, 1991, pp. 464–467, Guth J. et al., "Addressing the North American Trend Toward Low VOC Hair Sprays".

*Primary Examiner*—Edward J. Webman
*Attorney, Agent, or Firm*—Jane E. Gennaro

[57] ABSTRACT

Hair fixative carboxylated polymers are stabilized in an aqueous emulsion by neutralization with a cosmetically acceptable organic or inorganic base, require no organic solvent, no propellant when dispensed in non-aerosol containers, and minimal organic propellant when dispensed in aerosol containers.

14 Claims, No Drawings

– 5,501,851 –

EMULSION POLYMERS FOR USE IN HAIR FIXATIVES

This application is a continuation of application Ser. No. 07/915,488, filed Jul. 16, 1992 abandoned.

FIELD OF THE INVENTION

This invention pertains to hair fixative emulsion polymers that include carboxylic acid monomers that are partially or fully neutralized with standard cosmetically acceptable bases.

BACKGROUND OF THE INVENTION

Most aerosol hair spray systems in current use comprise a hair fixative polymer that is dissolved in ethanol or isopropanol, and an aerosol propellant that is usually a volatile hydrocarbon. These systems are becoming less acceptable because of consumer perception that alcohol in hair care products can dry or damage the hair, and because of environmental regulations controlling the emission of volatile organic compounds into the atmosphere. These factors have prompted the search for hair fixative delivery systems based on water and for hair fixative polymers dispersible in water.

U.S. Pat. Nos. 4,798,721 issued on 17 Jan. 1989, and 4,985,239 issued on 15 Jan. 1991, both assigned to Kao Corporation, Tokyo, Japan, disclose hair cosmetic compositions comprising a particulate latex polymer of water insoluble polymers that is selected from the group consisting of polystyrenes, copolymers of styrene with at least one vinyl monomer other than styrene, polyamides, polyurethanes, epoxy resins, and polymethyl methacrylates. It is stated that these polymers can be dispersed in water with a nonionic surfactant that is present in an amount up to 20% by weight of the monomers. Surfactants, however, act as plasticizers and humectants and tend to reduce high humidity curl retention capabilities of the hair fixatives.

Therefore, there is still a need for water based systems of hair fixative polymers that are alternatives to alcohol based systems and that exhibit all the characteristics of good hair fixatives, namely, holding power, humidity resistance, stiffness, clarity, aesthetics, and easy removability.

SUMMARY OF THE INVENTION

This invention is an aqueous based emulsified hair fixative composition that comprises by weight (A) 2%–15% of a carboxylated polymer comprising polymerized residues of (a) one or more acidic monomers, each containing one or more available carboxyl groups, present in an amount of 5%–35% by weight of the polymer; (b) one or more water insoluble comonomers present in an amount of 65%–95% by weight of the polymer; (c) optionally, up to 20% by weight of one or more water soluble monomers; and (B) an effective amount of a cosmetically acceptable organic or inorganic base to neutralize a sufficient proportion of the available carboxyl groups to obtain shampoo removability of the hair fixative composition without destabilizing the emulsion or dissolving the polymer. Optionally, the emulsion may contain a small amount of suitable surfactant, up to 4% by weight of the polymer solids of the hair fixative formulation.

DETAILED DESCRIPTION OF THE INVENTION

U.S. Pat. Nos. 3,810,977 and 3,927,199 disclose carboxylated resins, prepared by bulk, suspension or solution polymerization techniques that are suitable for use in hair cosmetics. These polymers are in the form of solid beads or pearls and typically have been formulated into alcohol based hair fixatives. It is now discovered that these and similar polymers can be dispersed in an aqueous emulsion and be effective in hair fixative compositions without the need for alcohol as a solvent.

The use of these polymers in a stabilized emulsion permits the achievement of high solids at low viscosity. A high solids content supplies an effective amount of polymer to the hair in a minimum amount of water to obtain good holding power. Low viscosity permits effective atomization of the emulsion at the spray nozzle. Thus, a hair fixative product suitable for use in either aerosol or nonaerosol formulations is achieved by controlling the solids content, viscosity, and particle size of the emulsion.

The polymers of this invention comprise monomers that contain one or more available carboxyl groups and that are present in an amount of 5%–35% by weight of the polymer, one or more water insoluble comonomers that are present in an amount of 65%–95% by weight of the polymer, and optionally one or more water soluble comonomers that are present in an amount up to 20% by weight of the polymer.

Monomers that contain one or more available carboxyl groups and that are suitable for use in the polymers of this invention are the $C_3$–$C_{12}$ mono- or dicarboxylic acids, such as, acrylic acid, methacrylic acid, crotonic acid, itaconic acid, maleic acid, fumaric acid, and the $C_1$–$C_8$ alkyl half esters of maleic and fumaric acids, such as methyl hydrogen maleate and butyl hydrogen fumarate, any other acidic monomers that are capable of being copolymerized with the particular desired interpolymer system, and combinations of those. The preferred carboxyl containing monomers are acrylic acid, crotonic acid, and monoisopropyl maleate.

The water insoluble comonomers suitable for use with the carboxyl containing monomers are $C_3$–$C_{12}$ acrylates and methacrylates; $C_1$–$C_8$ alkyl substituted acrylamides and methacrylamides; vinyl esters of $C_3$–$C_{12}$ carboxylic acids, styrene, and combinations of them. The preferred water insoluble comonomers are vinyl acetate, vinyl pivalate, vinyl neodecanoate, methyl methacrylate and t-octyl acrylamide.

The nonionic water soluble comonomers suitable for use in the polymers are one or more of water soluble hydroxyalkyl esters of acrylic and methacrylic acids, ($C_1$–$C_4$) alkyl ($C_2$–$C_4$) aminoalkyl esters of acrylic and methacrylic acids, acrylamide, methacrylamide, dimethyl acrylamide, dimethyl methacrylamide, vinyl caprolactam, and N-vinyl pyrrolidone. The preferred water soluble comonomers are hydroxypropyl methacrylate and hydroxyethyl methacrylate.

The emulsions may be prepared directly via emulsion polymerization or by post-emulsification of solvent-borne polymer solutions. Suitable surfactants, such as Triton X 305 and Triton X 301, products of Rohm and Haas, Philadelphia, Pa., and Abex 18S and Abex 26S, products of Alcolac, Baltimore, Md., and Sipon WD, a product of Rhone-Poulenc, Cranbury, N.J., are commercially available and can be used in these systems. When utilized, the surfactant may be present in amounts up to 4% by weight of the polymer solids.

The hair fixative formulations of this invention are prepared by diluting the polymer emulsions with water to 2%–15% solids content by weight, preferably 5%–10% by weight, and neutralizing a percentage of the free acidity of the carboxyl groups with a cosmetically acceptable organic or inorganic base, or a combination of those bases, to stabilize the emulsion and to make the polymer easily removable from the hair with shampoo. The amount of base used for neutralization is dependent on the hydrophobicity of the hair fixative polymer. The higher the carboxylic acid content of the polymer, the less the degree of neutralization required to impart water solubility. Conversely, the lower the carboxylic acid content, the greater the degree of neutralization required for water solubility. Nevertheless, if the polymer is neutralized to too great an extent, it may dissolve and destabilize the emulsion. Therefore, the degree of water solubility desired must be balanced against stabilization of the emulsion. This balance is achieved for the hair fixative polymers of this invention by neutralizing the available carboxyl groups present on the polymer to the equivalent on a molar basis of about 25%–100%. Suitable bases for neutralization of the polymer and stabilization of the polymer emulsion are the standard cosmetically acceptable bases known and used in the art. The preferred bases are sodium hydroxide, potassium hydroxide, 2-amino-2-methyl-1-propanol, histidine, tris(hydroxymethyl)aminomethane, and triethanolamine. The choice of the base and the degree of neutralization also affect the flexibility of the resultant hair fixative when sprayed on the hair, giving a soft or a hard hold. The choice of which base to utilize and the degree of neutralization required to achieve flexibility is within the expertise of one skilled in the art.

Although the hair fixative formulations of this invention are designed to be aqueous systems without the need for any organic solvent, an organic solvent may be admixed with the formulation if a quicker drying formulation is desired. The amount and choice of organic solvent used will depend on the desired end product formulation and is within the expertise of one skilled in the art. A propellant may also be used when it is desired to deliver the hair fixative formulation in an aerosol delivery system. In some instances, the propellant may also function as a solvent. Suitable solvents are alcohols and ketones, such as, ethanol, isopropanol, acetone, and methyl ethyl ketone, and combinations of those. Suitable propellants are ethers, compressed gases, halogenated hydrocarbons and hydrocarbons.

The following examples illustrate representative emulsification procedures for suitable carboxylated hair fixative polymers, and formulations for hair fixatives prepared from those polymers. Each of the emulsions was prepared into an aerosol and a nonaerosol formulation to determine its stability in those formulations. All of the nonaerosols were tested for curl retention, and the aerosols from the emulsions of Examples 1, 2, 3, and 6 were independently and variously tested for subjective qualities.

EMULSIFICATON PROCEDURES

Example 1

This example describes the post-emulsification of a hair fixative polymer containing residues of crotonic acid, vinyl acetate, and vinyl neodecanoate that is commercially available as Resyn® 28-2930 from National Starch and Chemical Company, Bridgewater, N.J. (The preparation of this polymer is discussed in U.S. Pat. No. 3,810,977.)

1. Equipment: A 5-liter, 4-neck round bottom flask equipped with steam injector, stainless steel stirrer, condenser, Dean Stark tube, and thermometer, and water baths for heating and cooling.

2. Material Charges:

|  | Grams |
|---|---|
| Initial Charge (IC) | |
| Resyn® 28-2930 | 600 |
| Ethyl acetate | 300 |
| Post Add-1 (PA-1) | |
| Water (Deionized) | 975 |
| Potassium hydroxide solution (25% w/v) | 78.4 |
| Resyn® 28-2930 | 12 |
| Post Add-2 (PA-2) | 15 |
| Dow Corning Antifoam 1510-US | |
| (10.0% solids) | |
| Post Add-3 (PA-3) | 7.5 |
| Dow Corning Antifoam 1510-US | |
| (10.0% solids) | |

3. Procedure: IC was placed in the reaction vessel and heated to reflux (78° C.). PA-1 was added all at once. When reflux was established, PA-2 was added all at once. When the reaction temperature reached 95.5° C., PA-3 was added all at once. Subsurface steam injection was started and the ethyl acetate was azeotropically removed. The contents were held at 100° C. for 15 minutes, cooled to 40° C. and filtered through 2 layers of cheese cloth.

4. Emulsion properties: 31.0% solids, 29.5 mPa.s (cps) Brookfield viscosity, 149–157 nm particle size, pH 6.5, 0.001% grit.

Example 2

This example describes the post-emulsification of a hair fixative polymer containing residues of methyl methacrylate, t-octyl acrylamide, hydroxypropyl methacrylate, t-butyl aminoethyl methacrylate, and acrylic acid that is commercially available as Amphomer® LV-71 from National Starch and Chemical Company, Bridgewater, N.J. (The preparation of this polymer is discussed in U.S. Pat. No. 3,927,199).

1. Equipment: A 3-liter, 4-neck round bottom flask equipped with steam injector, stainless steel stirrer, condenser, Dean Stark tube, and thermometer, and water baths for heating and cooling.

2. Material Charges:

|  | Grams |
|---|---|
| Initial Charge (IC) | |
| Amphomer® LV-71 | 200 |
| Isopropyl acetate | 88.3 |
| Ethanol | 85.7 |
| Post Add-1 (PA-1) | |
| Water (Deionized) | 400 |
| Potassium hydroxide solution (25% w/v) | 14.8 |
| Post Add-2 (PA-2) | 6.0 |
| Hydrolabs (NJ) Burst RSD10, defoamer | |
| (11.5% solids) | |

3. Procedure: IC was placed in the reaction vessel and heated to reflux (78° C.). PA-1 was added all at once. When the reaction temperature reached 90°– 92° C., PA-2 was added all at once. Subsurface steam injection was started and the isopropyl acetate and ethanol were azeotropically removed. When the temperature reached 100° C., the contents were cooled to 40° C. and passed through a 400 mesh stainless steel screen.

4. Emulsion properties: 20.8% solids, 20.0 mPa.s (CPS) Brookfield viscosity, 158–166 nm particle size, pH 6.1, 0.001% grit.

Example 3

This example describes the preparation of a hair fixative polymer emulsion from methyl methacrylate, butyl acrylate, methacrylic acid, and hydroxyethyl methacrylate by solution polymerization and subsequent post-emulsification. (Preparation of this polymer via emulsion polymerization is described in Example 4.)

A. Solution Polymer

1. Equipment: A 2-liter, 4-neck round bottom flask equipped with steam injector, stainless steel stirrer, condenser, Dean Stark tube, addition funnels, and a thermometer, and water baths for heating and cooling.

2. Material Charges:

|  | Grams |
| --- | --- |
| Monomer Mix |  |
| Butyl acrylate | 50 |
| Methyl methacrylate | 94 |
| Hydroxyethyl methacrylate | 20 |
| Methacrylic acid | 36 |
| Ethanol | 53.3 |
| Initial Charge (IC) |  |
| Benzoyl peroxide (78%) | 2 |
| Monomer mix | 38 |
| Isopropyl acetate | 42 |
| Slow Add-1 (SA-1) | 215 |
| Monomer mix |  |
| Slow Add-2 (SA-2) |  |
| Ethanol | 39 |
| Benzoyl peroxide solution (78 w/v %) | 1 |
| Slow Add-3 (SA-3) |  |
| Isopropyl acetate | 41.4 |
| Benzoyl peroxide solution (78 w/v %) | 1.5 |
| Diluent |  |
| Ethanol | 18 |
| Isopropyl acetate | 2 |
| Post Add (PA) |  |
| Water (deionized) | 326 |
| Sodium hydroxide solution (25% w/v) | 5 |

3. Procedure: The monomer mix was prepared first and charged to an addition funnel. IC was added to the reaction vessel, the contents heated to reflux (78° C.) and held at reflux for 15 minutes. SA-1 was added over 4 hours. After SA-1 had been added for 2 hours, SA-2 was started and added over 2 hours. When SA-1 and SA-2 were complete, the reaction contents were held at reflux for 30 minutes. SA-3 was started and added over 3 hours. At the completion of SA-3, the contents were held for 5 hours and then cooled to 60° C. The diluent was added and the contents heated to reflux. PA was added all at once. Solvent was distilled off until the reaction temperature reached 90° C. Subsurface steam injection was started and the ethanol and isopropyl acetate azeotropically removed to give the polymer in bead form. The polymer slurry was held at 100° C. for 15 minutes, cooled to 40° C., filtered and washed. The beads were dried at 60° C.

B. Post-Emulsion

1. Equipment: A 3-liter, 4-neck round bottom flask equipped with steam injector, stainless steel stirrer, condenser, Dean Stark tube and thermometer, and water baths for heating and cooling.

2. Material Charges:

|  | Grams |
| --- | --- |
| Initial Charge (IC) |  |
| Polymer (prepared in A.3 above) | 100 |
| Isopropyl acetate | 44 |
| Ethanol | 43 |
| Post Add-1 (PA-1) |  |
| Water (deionized) | 200 |
| Potassium hydroxide solution (25% w/v) | 12.5 |
| Post Add-2 (PA-2) | 1.6 |
| Hydrolabs Burst RSD-10, defoamer (11.5% solids) |  |
| Post Add-3 (PA-3) | 1.6 |
| Hydrolabs Burst RSD-10, defoamer |  |

3. Procedure: IC was placed in the reaction vessel and heated to reflux (78° C.). PA-1 was added all at once. When the reaction temperature reached 90° C., subsurface steam injection was started. At 93° C. PA-2 was added all at once. The subsurface steam injection was continued until the reaction temperature reached 100° C. PA-3 was added all at once and the contents held at 100° C. for 15 minutes. The contents were cooled to 60° C., and filtered through a 400 mesh stainless steel screen.

4. Emulsion properties: 22.8% solids, 143–151 nm particle size, pH 6.8, 0.008% grit.

Example 4

This example describes the preparation of a hair fixative polymer from methyl methacrylate, butyl acrylate, hydroxyethyl methacrylate and methacrylic acid by emulsion polymerization using a procedure given in U.S. Pat. No. 4,196,190 issued to Gehman et al. and assigned to Rohm and Haas Company, Philadelphia, Pa. The preparation of this polymer emulsion by solution polymerization and post-emulsification is described in Example 3.

1. Equipment: A 2-liter, 4-neck round bottom flask equipped with addition pump, condenser, stirrer, thermometer, addition funnels, nitrogen sparge, and water baths for heating and cooling.

2. Material Charges

|  | Grams |
| --- | --- |
| Emulsion Premix |  |
| Deionized water | 106.0 |
| Rhone-Poulenc Sipon WD | 3.8 |
|  | (at 29% solids) |
| Butyl acrylate | 93.8 |
| Methyl methacrylate | 176.0 |
| Hydroxyethyl methacrylate | 37.5 |
| Bromotrichloromethane | 7.0 |
| Methacrylic acid | 67.5 |
| Initial Charge-1 (IC-1) |  |
| Deionized water | 439.0 |
| Rhone-Poulenc Sipon WD | 2.8 |
| Initial Charge-2 (IC-2) | 32.5 |
| Emulsion premix |  |

|  | Grams |
| --- | --- |
| Initial Charge-3 (IC-3) | |
| Ammonium persulfate | 0.75 |
| Deionized water | 12.5 |
| Slow Add | 459.1 |
| Emulsion premix | |
| Post Add-1 (PA-1) | |
| t-Butyl hydroperoxide (70% solids) | 0.17 |
| Deionized water | 12.5 |
| Post Add-2 (PA-2) | |
| iso-Ascorbic acid | 0.22 |
| Deionized water | 12.5 |

3. Procedure: The emulsion premix was prepared first. The Sipon WD was added to the water, and the remaining ingredients were sequentially added and emulsified after each addition.

IC-1 was charged to the reaction vessel and placed under nitrogen sparge. The system was stirred and heated to 83° C. IC-2 was added and the system stirred for 5 minutes. IC-3 was added, the system reached 85.5° C., and was held at this temperature for 15 minutes. The system was cooled to 85° C. and held at that temperature during the remainder of the reaction. SA was added over 30 minutes and the system held for 1.5 hours. PA-1 and PA-2 were added, and the system held at 85° C. for 45 minutes. The reaction contents were cooled to 25° C. and filtered.

4. Emulsion properties: 39.2% solids, 272–280 nm particle size, 0.003% grit, and 11 mPa.s Brookfield viscosity.

Example 5

This example describes the preparation of a hair fixative polymer from methyl methacrylate, t-octyl acrylamide, hydroxypropyl methacrylate, and acrylic acid by emulsion polymerization.

1. Equipment: A 1-liter 4-neck round bottom flask equipped with stainless steel stirrer, condenser, thermometer, addition funnels, nitrogen sparge, and a water bath.

2. Material Charges:

|  | Grams |
| --- | --- |
| Initial Charge-1 (IC-1) | |
| Water | 219 |
| Rhone-Poulenc Sipon WD (29%) | 1.4 |
| Initial Charge-2 (IC-2) | |
| t-octyl acrylamide | 5.0 |
| Methyl methacrylate | 3.9 |
| Initial Charge-3 (IC-3) | |
| Ammonium persulfate | 0.38 |
| Water | 6.3 |
| Slow Add-1 (SA-1) | |
| t-octyl acrylamide | 70 |
| Methyl methacrylate | 54.3 |
| Hydroxypropyl methacrylate | 9.4 |
| Acrylic acid | 37.5 |
| Bromotrichloromethane | 1.9 |
| Slow Add-2 (SA-2) | |
| Water | 48.0 |
| Rhone-Poulenc Sipon WD (29%) | 1.9 |
| Alcolac Abex 18 S (35%) | 20.5 |
| Post Add-1 (PA-1) | |
| t-Butyl hydroperoxide | 0.12 |
| Water | 6.3 |
| Post Add-2 (PA-2) | |
| Iso-ascorbic Acid | 0.11 |
| Water | 6.25 |

3. Procedure: IC-1 was charged to the reaction vessel, heated to 83° C., and sparged with nitrogen. IC-2 was added, the reaction temperature rose to 85° C., and the contents were held at this temperature for 15 minutes. SA-1 and SA-2 simultaneously were added over 100 minutes, and the contents held at 85° C. for 1 hour. PA-1 and PA-2 were added, and the contents held at 85° C. for 15 minutes, cooled and filtered through two layers of cheese cloth.

4. Emulsion properties: 39.0% solids, 0.299 intrinsic viscosity, 18 mPa.s Brookfield viscosity, 236–244 nm particle size, pH 1.83, and 0.004% grit.

Example 6

This example describes the preparation of a solution polymer from vinyl neodecanoate, vinyl acetate, and monoisopropyl maleate, and subsequent post emulsification.

A. Solution Polymer

1. Equipment: A 2-liter, 4-neck round bottom flask equipped with steam injector, addition funnels, stainless steel stirrer, condenser, thermometer, and Dean Stark tube, and water baths for heating and cooling.

2. Material Charges:

|  | Grams |
| --- | --- |
| Monomer Mix | |
| Vinyl neodecanoate | 80 |
| Vinyl acetate | 60 |
| Monoisopropyl maleate | 60 |
| Initial Charge (IC) | |
| Monomer mix | 20 |
| Ethyl acetate | 80 |
| t-Butyl peroctoate solution (50% w/v) | 1.70 |
| Slow Add-1 (SA-1) | 180 |
| Monomer mix | |
| Slow Add-2 (SA-2) | |
| Ethyl acetate | 80 |
| t-Butyl peroctoate solution (50% w/v) | 5.2 |
| Slow Add-3 (SA-3) | |
| Ethyl acetate | 30 |
| t-Butyl peroctoate solution (50% w/v) | 1.70 |
| Diluent | 10 |
| Ethyl acetate | |
| Post Add (PA) | |
| Water | 200 |
| Polyvinyl alcohol | 0.32 |

3. Procedure: The monomer mix was prepared and charged to an addition funnel. IC was added to the reaction vessel and the contents heated at reflux (78° C.) for 15 minutes. SA-1 was started and added over 4 hours, and SA-2 was started and added over 4.5 hours. When SA-1 and SA-2 were complete, the contents were held at reflux for 2 hours. SA-3 was started and added over 1 hour. At the completion of SA-3, the contents were held for 2 hours and then cooled to 60° C. The diluent was added and the contents heated to reflux. PA was added all at once. The solvent was distilled off until the reaction temperature reached 90° C. Subsurface steam injection was started and the ethyl acetate azeotropically removed to give the polymer in bead form. The polymer slurry was held at 100° C. for 15 minutes, cooled to 40° C., filtered and washed. The beads were dried at 60° C.

B. Post-Emulsion

1. Equipment: A 1-liter round bottom flask equipped with stainless steel stirrer.

2. Procedure: The polymer beads (5 grams) were dissolved in 94.1 grams of water and 0.9 gram of 2-amino-2-methyl-1-propanol with stirring until emulsified.

Example 7

This example describes the preparation of a hair fixative polymer from styrene by emulsion polymerization using a procedure given in U.S. Pat. No. 4,798,721 issued to Yahagi et al. and assigned to Kao Corporation of Japan.

1. Equipment: A 2-liter round bottom flask equipped with a stainless steel stirrer, condenser, thermometer, addition funnels, nitrogen sparge, and water bath.

2. Material Charges:

|  | Grams |
|---|---|
| Initial Charge (IC) | |
| Distilled water | 500 |
| Polyoxyethylene (30) nonylphenyl ether | 25 |
| ammonium persulfate | 1.2 |
| Slow Add (SA) styrene | 125 |

3. Procedure: IC was charged to the reaction flask and the flask was sparged with nitrogen. The contents were heated to 62° C. and held at that temperature for the remainder of the reaction. SA was added over 2 hours, and the reaction was held for an additional 6 hours.

4. Emulsion properties: 22% solids, 106–114 nm particle size, pH 2.12, 0.002% grit.

Example 8

This example describes the preparation of a hair fixative polymer from styrene and sodium styrene sulfonate by emulsion polymerization using a procedure given in U.S. Pat. No. 4,798,721 issued to Yahagi et al. and assigned to Kao Corporation of Japan.

1. Equipment: A 2-liter round bottom flask equipped with a stainless steel stirrer, condenser, thermometer, addition funnel, nitrogen sparge, and water bath.

2. Material Charges:

|  | Grams |
|---|---|
| Initial Charge (IC) | |
| Distilled water | 500 |
| Polyoxyethylene (30) nonylphenyl ether | 25 |
| Ammonium persulfate | 1.2 |
| Slow Add (SA) | |
| Styrene | 117.5 |
| Sodium styrene sulfonate | 7.5 |

Procedure: IC was charged to the reaction flask and the flask was sparged with nitrogen. The contents were heated to 62° C. and held at that temperature for the remainder of the reaction. SA was added over 2 hours, and the reaction was held for an additional 6 hours.

4. Emulsion properties: 22.3% solids, 32–40 nm particle size, 0.000% grit.

Example 9

This example describes the preparation of a hair fixative polymer containing residues of styrene, trimethylaminoethyl methacrylate chloride, and polyoxyethylene nonylphenyl ether (average 30 addition moles of ethylene oxide) by emulsion polymerization using a procedure given in U.S. Pat. No. 4,798,721 issued to Yahagi et al. and assigned to Kao Corporation of Japan.

1. Equipment: A 2-liter round bottom flask equipped with a stainless steel stirrer, condenser, thermometer, addition funnels, nitrogen sparge, and water bath.

2. Material Charges:

|  | Grams |
|---|---|
| Initial Charge (IC) | |
| Distilled water | 500 |
| Polyoxyethylene (30) nonylphenyl ether | 25 |
| Ammonium persulfate | 1.2 |
| Slow Add (SA) | |
| Styrene | 117.5 |
| Trimethylaminoethyl methacrylate chloride | 7.5 |

3. Procedure: IC was charged to the reaction flask and the flask was sparged with nitrogen. The contents were heated to 62° C. and held at that temperature for the remainder of the reaction. SA was added over 2 hours, and the reaction was held for an additional 6 hours.

4. Emulsion properties: 21.8% solids, 75–83 nm particle size, 0.002% grit.

Non-aerosol Formulations

The emulsions from Examples 1–9 were diluted with water to 10% polymer solids by weight and a percentage of the free acidity neutralized to prepare nonaerosol hairspray formulations. The percentage neutralization was determined on the basis of the carboxylic acid monomer content of the polymer. Example 6 was neutralized to 100% with 2-amino-2-methyl-1-propanol and remained stable as an emulsion. The percentage neutralization and the neutralizing agent for each of the Examples are shown in Table 1.

TABLE 1

NON-AEROSOL FORMULATIONS

| Example | % Free Acidity Neutralized | Neutralizing Agent |
|---|---|---|
| 1 | 50 | histidine |
| 2 | 60 | histidine |
| 3 | 60 | histidine |
| 4 | 44 | KOH |
|   | 33.6 | histidine |
| 5 | 50 | KOH |
| 6 | 100 | 2-amino-2-methyl-1-propanol |
| 7 | none | |
| 8 | none | |
| 9 | none | |

Curl Retention of Nonaerosol Formulations

Each of the nonaerosol formulations prepared from the emulsions of Examples 1 to 9 was tested on nine swatches of strands of Remi Blue String European Brown hair for curl retention at 90% relative humidity, 22° C. (72° F.), and the results pooled and averaged. The testing procedure was as follows:

The hair was separated into swatches of approximately 2 grams in weight and bound at one end with cotton thread and epoxy glue. Each swatch was then washed in a 10% solution of shampoo, and rinsed in warm tap water. The hair was cut into 6 inch lengths from the secured end and dried at 49° C. (120° F.). It was wet again and combed, and the excess water squeezed out. The hair swatch was then rolled and secured onto a ½ inch diameter Teflon® mandrel, and dried at 49° C. (120° F.). When dried, it was removed from the mandrel and the resulting curl suspended by its bound end. For each swatch, the curl height was measured, and then the curl was sprayed uniformly with four sprays of nonaerosol formulation. The curl was laid on a horizontal surface and allowed to air dry for one hour. The dried curl was then resuspended and set into a chamber at 22° C. (72° F.), 90% relative humidity, and the curl height measured immediately, and at 15, 30, 60 minute, and 2, and 5 hour intervals.

The percentage curl retention was calculated by the formula $(L-L')/(L-L^o) \times 100$, where L is the length of hair fully extended, $L^o$ is the length of hair before spray and exposure, and $L'$ is the length of hair after spray and exposure.

The percentage loss in curl retention was calculated by the formula $(T^o - T')/T^1 \times 100$, where $T^o$ is the percent curl retention at 15 minutes and $T'$ is the percent curl retention at 5 hours.

The results are set out in Table 2 and show that the hair fixative polymers and the nonaerosol formulations prepared from the polymers according to the methods of Examples 1, 2, 3, 4, and 5 effectively retained curl, showing only between 4%–8% loss of curl retention after five hours under the test conditions. These Examples contained less than 4% surfactant by weight of polymer solids.

The emulsion from Example 6 would also be expected to exhibit effective curl retention; however, the free acidity of the polymer was neutralized to 100% to test the stability of the emulsion at the extreme of neutralization. While the emulsion remained stable, the lack of effective curl retention at 100% neutralization demonstrates that the degree of neutralization must be balanced to achieve stability, shampoo removability, and also effective hair fixative properties.

The nonaerosol formulations prepared from the emulsions of Examples 7, 8, and 9 did not effectively retain curl, showing a loss of curl retention of 15%–29% after five hours under the test conditions. These emulsions contained approximately 16%–17% surfactant by weight of polymer solids. Inasmuch as surfactants act as humectants, the loss of curl retention in these Examples is thought to be a result of the level of surfactant needed to prepare the emulsions of these Examples, demonstrating that this level can be detrimental to the properties needed for a good hair fixative formulation.

TABLE 2

PERCENTAGE CURL RETENTION AT 90% RELATIVE HUMIDITY, 22° C. (72° F.) FOR NON-AEROSOL HAIRSPRAYS

| SAMPLE | 15 MIN | 30 MIN | 60 MIN | 2 HR | 5 HR | % LOSS |
|---|---|---|---|---|---|---|
| 1 | 90.0 | 84.6 | 83.6 | 83.6 | 82.8 | 8 |
| 2 | 95.2 | 92.2 | 89.4 | 87.6 | 87.6 | 7 |
| 3 | 95.7 | 94.9 | 93.4 | 92.6 | 91.1 | 4 |
| 4 | 96.4 | 95.6 | 93.3 | 93.3 | 91.9 | 4 |
| 5 | 94.4 | 92.2 | 91.4 | 89.0 | 88.2 | 6 |
| 6 | 88.3 | 86.6 | 80.1 | 78.6 | 70.8 | 19 |
| 7 | 73.3 | 64.9 | 57.5 | 53.3 | 51.4 | 29 |
| 8 | 89.3 | 83.7 | 79.6 | 78.8 | 71.3 | 20 |
| 9 | 89.6 | 80.9 | 79.9 | 75.8 | 75.8 | 15 |

Aerosol Formulations

The emulsions from Examples 1–9 were diluted with water to 5%–10% solids content by weight, and a percentage of the free acidity was neutralized to prepare aerosol hairspray formulations. Dimethyl ether (DME) was added to make a final concentration of 30% DME by weight. The percentage solids content, the percentage neutralization, and the neutralizing base are shown in Table 3.

TABLE 3

AEROSOL FORMULATIONS

| Example | % Solids Content | % Free Acidity Neutralized | Neutralizing Base |
|---|---|---|---|
| 1 | 10 | 50 | histidine |
| 2 | 10 | 60 | histidine |
| 2 | 7 | 60 | histidine |
| 3 | 5 | 60 | histidine |
| 4 | 5 | 44 | KOH |
|   |   | 33.6 | histidine |
| 5 | 7 | 50 | KOH |
| 6 | 10 | 100 | 2-amino-2-methyl-1-propanol |
| 7 | Not stable in water and dimethyl ether | | |
| 8 | 0.2 | | |
| 9 | Not stable in water and dimethyl ether | | |

Subjective Properties of Aerosol Formulations

Examples 1, 2, 3, and 6 of the aerosol formulations were evaluated on 10 inch long, 2 gram swatches of brown hair by a panel of 8 persons. Each panel member evaluated a test swatch treated with one of the example formulations and a control swatch treated with a control formulation for each of the characteristics of stiffness, resistance to combing, flake accumulation, gloss, static, length of time of initial tackiness, drying time, and shampoo removability. The panel member rated both the test swatch and the control swatch by a numerical performance rating, and equivalent ratings were not permitted. In the evaluations, stiffness was superior to softness; no resistance to combing was superior to resistance; no flake accumulation on hair and comb was superior to flake accumulation; gloss was superior to lack of gloss; no static flyaway after combing was superior to static flyaway; a shorter time of tackiness was superior to a longer time; a shorter drying time was superior to a longer drying time; and complete removal after two shampoos was superior to incomplete removal needing more washings. A total of 8 repeats per sample were made. The panel results were analyzed statistically and summarized comparing the test swatch as superior to, equivalent to, or inferior to, the control swatch. The results of the panel evaluations are set out in Table 2 and show that the aqueous aerosol formulations perform for most properties comparably to the ethanol based systems and are effective alternatives to ethanol based systems.

TABLE 4

| | EMULSION STABILITY | | |
|---|---|---|---|
| Time | Starting emulsion pH | 60% Neutralized with Histidine | 25% Neutralized with NaOH |
| Example 2 at 10% polymer solids - pH vs. time at 49° C. (120° F.) | | | |
| Initial | 6.10 | 6.55 | 6.58 |
| 2 weeks | 6.10 | 6.32 | 6.34 |
| 4 weeks | 6.10 | 6.30 | 6.32 |
| 6 weeks | 6.09 | 6.30 | 6.30 |
| 8 weeks | 6.09 | 6.30 | 6.30 |
| 9 weeks | 6.05 | *6.27 | **6.26 |
| 11 weeks | 6.06 | 6.30 | 6.26 |
| 12 weeks | 6.03 | 6.27 | 6.26 |
| 14 weeks | 6.02 | 6.26 | 6.26 |
| 18 weeks | 6.02 | 6.26 | 6.26 |
| 19 weeks | 6.02 | 6.25 | 6.26 |

TABLE 4

| SUBJECTIVE PROPERTIES OF AEROSOL HAIRSPRAY FORMULATIONS | | | | | | | | | |
|---|---|---|---|---|---|---|---|---|---|
| Example | % solids | Control | Stiffness | Combing Ease | Flake | Gloss | Static | Tack Time | Drying Time | Shampoo Removability |
| 1 | 10% | 2[a] | + | = | − | = | = | | | = |
| 1 | 10% | 1[b] | − | + | = | − | − | + | + | |
| 2 | 10% | 2[a] | = | = | − | = | − | | | = |
| 2 | 10% | 2[b] | − | + | + | − | − | + | + | |
| 2 | 7% | 2[a] | + | = | = | = | = | = | = | |
| 2 | 7% | 2[b] | = | + | + | − | − | = | − | |
| 3 | 5% | 3[a] | = | = | + | = | = | | | |
| 6 | 5% | 2[a] | = | = | = | = | = | − | − | |
| 6 | 7.5% | 2[a] | = | = | = | = | = | − | − | |

+ sample superior to control
− sample inferior to control
= no significant difference
Control 1[b]: The polymer beads of Example 1, before post-emulsification, were dissolved at 5% polymer solids by weight in anhydrous alcohol, 90% of the free acidity was neutralized with 2-amino-2-methyl-1-propanol, and 30% by weight of a hydrocarbon blend (80% isobutane/20% propane) was added as propellant.
Control 2[b]: The polymer beads of Example 2, before post-emulsification, were dissolved at 5% polymer solids by weight in anhydrous alcohol, 90% of the free acidity was neutralized with 2-amino-2-methyl-1-propanol, and 30% by weight of a hydrocarbon blend (80% isobutane/20% propane) was added as propellant.
Control 2[a]: The polymer beads of Example 2, before post-emulsification, were dissolved at 5% polymer solid, by weight in water, 90% of the free acidity was neutralized with 2-amino-2-methyl-1-propanol, 0.5% by weight of a commercial defoamer was added, and 33% by weight dimethyl ether was added as propellant.
Control 3[a]: The polymer beads of Example 3, before post-emulsification, were dissolved at 5% polymer solids by weight in water, 90% of the free acidity was neutralized with 2-amino-2-methyl-1-propanol, and 30% by weight dimethyl ether was added as propellant.

Stability

Neutralization of the polymers of this invention is necessary in order to (1) form the emulsion, and (2) impart shampoo removability. The degree of neutralization required is a function of the carboxylic acid content of the polymer and, in general, the polymers of this invention have a carboxylic acid content that will require neutralization from about 25% to 100% of the available carboxyl groups. Two samples of Example 2 at 10% polymer solids by weight were neutralized, one neutralized 60% with histidine, and the second neutralized 25% with NaOH, and the pH of these two samples monitored over a period of weeks at 49° C. (120° F.) and at room temperature. The results are set out in Table 4 and show that overall the pH of the samples remained relatively constant, indicating that the Example 2 emulsion was stable over time.

TABLE 4-continued

| | EMULSION STABILITY | | |
|---|---|---|---|
| Time | Starting emulsion pH | 60% Neutralized with Histidine | 25% Neutralized with NaOH |
| Example 2 at 10% polymer solids - pH vs. time at room temperature | | | |
| Initial | 6.10 | 6.55 | 6.58 |
| 19 weeks | 6.06 | 6.42 | 6.48 |

*turned from opaque white to golden yellow
**turned from opaque white to translucent white Those skilled in the art will recognize, or be able to ascertain using no more than routine experimentation, many equivalents to the specific embodiments of the invention described specifically above. Such equivalents are intended to be encompassed in the scope of the following claims.

We claim:

1. A particulate dispersion of a polymer in water suitable for use as a hair fixative characterized in that the polymer
   (i) is present in an amount from 2% to 15% by weight,
   (ii) has a particle size from 32 nm to 280 nm,
   (iii) is prepared from
      (a) one or more ethylenically unsaturated acidic monomers, each containing one or more available carboxyl groups, present in an amount of 5%–35% by weight of the polymer and
      (b) one or more water insoluble comonomers present in an amount of 65%–95% by weight of the polymer, and
   (iv) is neutralized with one or more cosmetically acceptable organic or inorganic bases in an amount effective to make the polymer later removable with shampoo, but without destabilizing the particles.

2. The polymer of claim 1 prepared from acidic monomers selected from the group consisting of acrylic acid, methacrylic acid, crotonic acid, itaconic acid, maleic acid, fumaric acid, the $C_1$–$C_8$ alkyl half esters of maleic acid, the $C_1$–$C_8$ alkyl half esters of fumaric acid and combinations thereof.

3. The polymer of claim 2 in which the acidic monomers are acrylic acid, monoisopropyl maleate, and crotonic acid.

4. The polymer of claim 1 prepared from water insoluble comonomers selected from the group consisting of methyl methacrylate, t-octyl acrylamide, vinyl neodecanoate, and vinyl acetate.

5. The polymer of claim 1 neutralized with a cosmetically acceptable base selected from the group consisting of sodium hydroxide, potassium hydroxide, 2-amino-2-methyl-1-propanol, histidine, tris(hydroxymethyl)aminomethane, and triethanol amine.

6. The polymer of claim 1 in which the effective amount of base for neutralization is an amount to neutralize from about 25%–100% of the available carboxyl groups on the polymer.

7. The polymer of claim 1 in a hair fixative composition in which the hair fixative composition comprises a surfactant present in an amount up to 4% by weight of the polymer solids.

8. The polymer of claim 1 in a hair fixative composition in which the hair fixative composition comprises a propellant selected from the group consisting of ethers, compressed gases, halogenated hydrocarbons and hydrocarbons.

9. The polymer of claim 1 prepared additionally from up to 20% by weight of nonionic water soluble comonomers selected from the group consisting of water soluble hydroxyalkyl esters of acrylic and methacrylic acids, $C_1$–$C_4$ alkyl $C_2$–$C_4$ aminoalkyl esters of acrylic acid, $C_1$–$C_4$ alkyl $C_2$–$C_4$ aminoalkyl esters of methacrylic acid, acrylamide, methacrylamide, dimethyl acrylamide, dimethyl methacrylamide, N-vinyl pyrrolidone, vinyl caprolactam and combinations thereof.

10. The polymer of claim 9 in which the nonionic water soluble comonomers are hydroxypropyl methacrylate and hydroxyethyl methacrylate.

11. The polymer of claim 9 in a hair fixative composition in which the hair fixative composition comprises a surfactant present in an amount up to 4% by weight of the polymer solids.

12. The polymer of claim 9 in a hair fixative composition in which the hair fixative composition comprises a propellant selected from the group consisting of ethers, compressed gases, halogenated hydrocarbons and hydrocarbons.

13. A process for the preparation of a particulate dispersion of polymer in water suitable for use as a hair fixative comprising the steps of
   (A) preparing a polymer from
      (a) one or more ethylenically unsaturated acidic monomers, selected from the group consisting of $C_3$–$C_{12}$ mono-carboxylic acids, di-carboxylic acids, the $C_1$–$C_8$ alkyl half esters of maleic acid, the $C_1$–$C_8$ alkyl half esters of fumaric acid, present in an amount of 5%–35% by weight of the polymer; and
      (b) one or more water insoluble comonomers, selected from the group consisting of $C_3$–$C_{12}$ acrylates, $C_3$–$C_{12}$ methacrylates, $C_1$–$C_8$ alkyl substituted acrylamides, $C_1$–$C_8$ alkyl substituted methacrylamides, vinyl esters of $C_3$–$C_{12}$ carboxylic acids, styrene, and combinations thereof, present in an amount of 65%–95% by weight of the polymer; and
      (c) optionally, one or more nonionic water soluble comonomers selected from the group consisting of water soluble hydroxyalkyl esters of acrylic and methacrylic acids, $C_1$–$C_4$ alkyl $C_2$–$C_4$ aminoalkyl esters of acrylic acid, $C_1$–$C_4$ alkyl $C_2$–$C_4$ aminoalkyl esters of methacrylic acid, acrylamide, methacrylamide, dimethyl acrylamide, dimethyl methacrylamide, N-vinyl pyrrolidone, vinyl caprolactam, and combinations thereof, present in an amount up to 20% by weight of the polymer;
   (B) dispersing the polymer in water in the amount of 2% to 15% solids by weight with an effective amount of one or more cosmetically acceptable organic or inorganic bases to neutralize a sufficient proportion of the available carboxyl groups on the polymer to obtain a polymer with a particle size from 32 nm to 280 nm and to obtain shampoo removability of the polymer without destabilizing or dissolving the polymer particles.

14. The process according to claim 13 in which the particulate dispersion of polymer in water is prepared in the presence of a surfactant present in an amount up to 4% by weight of the polymer solids.

* * * * *